US008861904B2

(12) United States Patent
Erickson et al.

(10) Patent No.: US 8,861,904 B2
(45) Date of Patent: Oct. 14, 2014

(54) OPTOFLUIDIC APPARATUS, METHOD, AND APPLICATION

(75) Inventors: David Erickson, Ithaca, NY (US); Aram J. Chung, Ithaca, NY (US); Erica E. Jung, Ithaca, NY (US)

(73) Assignee: Cornell University, Ithaca, NY (US)

( * ) Notice: Subject to any disclaimer, the term of this patent is extended or adjusted under 35 U.S.C. 154(b) by 85 days.

(21) Appl. No.: 13/504,297

(22) PCT Filed: Oct. 27, 2010

(86) PCT No.: PCT/US2010/054231
§ 371 (c)(1),
(2), (4) Date: May 16, 2012

(87) PCT Pub. No.: WO2011/053626
PCT Pub. Date: May 5, 2011

(65) Prior Publication Data
US 2012/0269481 A1    Oct. 25, 2012

Related U.S. Application Data

(60) Provisional application No. 61/256,756, filed on Oct. 30, 2009.

(51) Int. Cl.
*G02B 6/26*      (2006.01)
*G01N 21/77*     (2006.01)
*G02B 6/35*      (2006.01)
*G02B 6/032*     (2006.01)

(52) U.S. Cl.
CPC ............ *G01N 21/7746* (2013.01); *G02B 6/354* (2013.01); *G02B 2006/0325* (2013.01)
USPC .......................................... 385/22; 385/135

(58) Field of Classification Search
CPC .................... G02B 6/354; G02B 2006/0325
USPC ........................................................ 385/22
See application file for complete search history.

(56) References Cited

U.S. PATENT DOCUMENTS

| 6,016,372 | A  | * | 1/2000 | Fein et al. ........................ 385/12 |
| 6,020,207 | A  | * | 2/2000 | Liu ............................... 436/164 |
| 6,360,775 | B1 | * | 3/2002 | Barth et al. .................... 137/828 |
| 6,408,112 | B1 |   | 6/2002 | Bartels |
| 6,542,231 | B1 | * | 4/2003 | Garrett .......................... 356/246 |
| 6,603,556 | B2 |   | 8/2003 | Belz |
| 6,687,429 | B2 |   | 2/2004 | Chung |
| 6,949,176 | B2 |   | 9/2005 | Vacca |

(Continued)

*Primary Examiner* — Charlie Peng
(74) *Attorney, Agent, or Firm* — William Greener; Bond, Schoeneck & King, PLLC (57) ABSTRACT

A reconfigurable optofluidic apparatus includes a microfluidic chip including a microfluidic channel further including an inlet for a liquid core waveguide fluid; a channel pathway for the liquid core waveguide fluid; a plurality of non-core waveguide fluid inlets; a switching chamber having a larger cross sectional area than the channel pathway; and an outlet for the liquid core waveguide fluid and non-core waveguide fluid, further including a plurality of non-liquid core waveguides disposed in the switching chamber. Light input to the apparatus propagates in the liquid core/liquid cladding (liquid) waveguide. The path of the liquid waveguide can be steered in a region of the apparatus over one of the non-liquid core waveguides such that the light is end-fire- or evanescently-coupled into the non-liquid core waveguide and output therefrom or between two of the non-liquid core waveguides and not coupled or output. Associated optofluidic switching methods are disclosed.

31 Claims, 6 Drawing Sheets

(56) References Cited

U.S. PATENT DOCUMENTS

| | | |
|---|---|---|
| 7,005,090 B2 | 2/2006 | Mueller |
| 7,155,082 B2 * | 12/2006 | Oakey et al. .................... 385/16 |
| 2001/0055546 A1 | 12/2001 | Weigl |
| 2002/0048425 A1 | 4/2002 | McBride |
| 2002/0182747 A1 | 12/2002 | Beebe |
| 2003/0012483 A1 | 1/2003 | Ticknor |
| 2003/0219197 A1 * | 11/2003 | Kawamoto ..................... 385/22 |
| 2005/0287696 A1 | 12/2005 | Dumais |
| 2009/0097808 A1 * | 4/2009 | Wolfe et al. .................. 385/125 |
| 2009/0230028 A1 | 9/2009 | Mueller |

* cited by examiner

OPTOFLUIDIC APPARATUS, METHOD, AND APPLICATION

RELATED APPLICATION DATA

The instant application claims priority to U.S. provisional patent application Ser. No. 61/256,756 filed on Oct. 30, 2009, the subject matter of which is herein incorporated by reference in its entirety.

BACKGROUND

Embodiments of the invention are directed to the field of optofluidics, particularly, to optofluidic apparatus, methods, and applications and, more particularly, to reconfigurable optofluidic apparatus, methods, and applications.

Reconfigurable systems are those in which some or all of a system's physical, chemical or electrical properties can be changed, either on-command to enhance functionality or autonomously in response to a change in external/internal conditions. Such systems are ubiquitous in nature and have recently been realized in a wide range of engineering applications including self-healing polymers, self-reproducing and dynamically reconfigurable robots, morphing aircraft, computing, and adaptive space structures. In electronics, the ubiquitous reconfigurable system is the Field Programmable Gate Array (FPGA), which is a semiconductor device that can be reprogrammed by the user at any time post-fabrication to perform any arbitrary set of logical functions. Such devices have brought a number of benefits particularly to military systems including, but not limited to, reduced cost (e.g., where relatively few pieces are required it is much cheaper to purchase and program off-the-shelf FPGAs than design an application specific integrated circuit) and increased security (e.g., FPGAs can be designed to self-erase the programmed circuitry making it difficult to reverse engineer captured devices). Despite the advantages demonstrated in the electronics' field and the importance of photonic systems to current and emerging applications, at present there is not an equivalently ubiquitous FPGA-type technology for photonics.

A recognized key requirement for reconfigurable optical systems is the ability to dynamically control either (1) the physical layout or (2) the refractive indices of the optical components. Recent advancements in optical MEMS technology have enhanced functionality and flexibility with regards to (1) but are fundamentally limited in the degree to which the systems can be manipulated (achievable physical displacements in MEMS are small and must be predefined) and greatly increase device fabrication complexity. With regards to (2), traditional techniques for manipulating the refractive index through the application of electric, acoustic, thermal, and mechanical strain fields are limited by the achievable $\Delta n/n$ (i.e., the achievable change in refractive index divided by the base refractive index). Optofluidic technology has the potential to offer an order of magnitude jump in this quantity over these existing approaches.

In addition to enabling rapid reconfigurability, optofluidic-based photonics technology may provide inherent advantages in terms of temperature stabilization due to the incorporation of liquids into the optical structure. In general the heat transfer coefficient (which is the proportionality constant between heat rejection and surface temperature) for systems immersed in air ranges from 10 $W/m^2K$ to 100 $W/m^2K$, whereas for liquids they are closer to 500 $W/m^2K$ to 10,000 $W/m^2K$. As such, it may be possible to decrease a device's temperature rise for a given heat rejection requirement by an order of magnitude (such that a 10° C. increase in temperature for a traditional device would result in a 1° C. increase in an optofluidic device. It has also recently been demonstrated that incorporation of liquids into a device structure can automatically compensate for thermo-optic effects. In addition, similar fluid based opto-electronic systems have demonstrated increased radiation resistance and, optical data storage densities as high as 33× that of the current Blu-ray standard.

Microfluidics can be defined as the study or use of the motion of fluids in confined systems where the fundamental length scale is between 100 nanometers (nm) and 1 millimeter (mm). In this context, modern microfluidics can be traced back to the development of a silicon chip-based gas chromatograph at Stanford University and the inkjet printer at IBM. However, the concept of the integrated microfluidic device as it is known today was not proposed until the early 1990s by Manz et al. Since that time the field has developed to a point where fluid flow and species transport on these scales can be accomplished by a number of elegant techniques, a few of which include: pressure driven flow, electrokinetics, buoyancy, magnetohydrodynamics, capillarity, electrowetting, and thermocapillarity.

It was earlier thought that the bioanalytical improvements associated with the scaling down of the size of these devices (which came to be known as labs-on-a-chip) would be the biggest advantage of these devices. Further developments however revealed other significant advantages including: minimized consumption of reagents, increased automation, thermal stabilization and reduced manufacturing costs. As a result of these advantages, the field has blossomed into many different areas ranging from biological and chemical analysis, point-of-care testing, clinical and forensic analysis, and molecular diagnostics. As embodied herein below, the advantages of microfluidics in terms of being able to shuttle chemicals around on a chip will be translated to shuttling light around.

The origin of the macroscopic liquid optical devices can be traced as far back as the 18th century. More recent advancement in microfluidic technology have enabled the development of present day equivalents of such devices centered on the marriage of microfluidics and optics. Since 2005, these efforts have matured into a new research field known as "optofluidics." Some of the more prominent examples of such devices include: liquid crystal infused photonic crystal lasers, fluid-fluid waveguides, florescent light sources, polarization independent fluidic switches, microfluidically tuned optical fiber and interferometers, electronic paper, high resolution in-chip lensless microscopy, and a variety of biomolecular sensor platforms and optical manipulation techniques.

Early on, reconfigurable photonics was viewed as one of the major applications of optofluidic technology. This led initially to the development of adaptable fluid optical lensing technologies using electrowetting based approaches. Later versions of these devices included planar lenses more practical for on-chip integration, reconfigurable waveguiding approaches, designs that enable focusing in three dimensions, and self-assembled minors using Janus particles. The advantage of these devices in the context of reconfigurable photonics vs. solid lenses was in their ability to simultaneously change the physical shape and refractive index profile of the lens (i.e., one could build a system that would allow for automatic refocusing and aberration correction).

In 2006, the first example of the use of nanofluidics to create reconfigurable silicon photonic crystals was reported. Traditionally refractive index modulation in silicon is limited to the exploitation of relatively weak non-linear material properties. As a result, devices require either long interaction lengths, high operational power, or the incorporation of resonant elements to enhance the effect. The use of these elements leads either to very large devices or low bandwidth. Two other limitations include long switching times and extension to greater degrees of adaptability. Since these systems required transport through a nanochannel, the hydrodynamics were such that only very low flow rates could be obtained, resulting in switching times on the order of 20 s. Moreover, the elements of a silicon photonic crystal must be extremely close packed (on the order of 350 nm periodicity) in order to maintain a full bandgap. As such, the development of a mechanical valving infrastructure to enable arbitrary flow routing poses an extreme fabrication and integration challenge.

The inventors have thus recognized advantageous and beneficial solutions to the aforementioned disadvantages and problems in the prior art via reconfigurable optofluidic apparatus and methods according to embodiments of the invention disclosed below.

SUMMARY

An embodiment of the invention is a reconfigurable optofluidic apparatus. The optofluidic apparatus includes a microfluidic chip including a microfluidic channel, wherein the microfluidic channel further includes an inlet for a liquid core waveguide fluid; a channel pathway for the liquid core waveguide fluid; a plurality of non-core waveguide fluid inlets; a switching chamber, wherein the switching chamber has a cross sectional area that is greater than a corresponding cross sectional area of the channel pathway; and an outlet for the liquid core waveguide fluid and non-core waveguide fluid, the optofluidic device further including a plurality of non-liquid core waveguides disposed at least in part in the switching chamber; and, a light input port. According to an aspect, the plurality of non-liquid core waveguides are solid core waveguides that are disposed in a parallel spaced relationship. According to non-limiting aspects, the plurality of non-liquid core waveguides include planar optical elements such as a waveguide, an optical ring resonator, an interferometer, a photonic crystal, and a photonic crystal resonator. The plurality of optical ring resonators may have at least two different ring sizes and may include circular, elliptical, racetrack, and other geometries. In an aspect, the plurality of non-core waveguide fluid inlets further includes a plurality of liquid waveguide focusing channels and a plurality of liquid waveguide steering channels. In an exemplary aspect, the microfluidic chip further includes a second microfluidic channel that further includes a second inlet for the liquid core waveguide fluid; a second channel pathway for the liquid core waveguide fluid; and a second plurality of non-core waveguide fluid inlets, wherein the second microfluidic channel is in fluid connection with the switching chamber. As well understood in the art, the fluid waveguide core fluid will have a higher index of refraction than the non-core (cladding) waveguide fluid. The core and cladding fluids may be miscible liquids (e.g., $CaCl_2$-core fluid, water-cladding fluid) or immiscible liquids (e.g., water-core fluid, Flourinert oil-cladding fluid). According to an aspect, the apparatus further includes an integrated, self-contained, immiscible core/cladding fluid recirculation system.

An embodiment of the invention is an optofluidic switching method. The optofluidic switching method includes the steps of inputting light into a core of a liquid core waveguide having a given propagation pathway that includes a steerable region; propagating the light in the liquid core waveguide; and coupling at least a portion of the light from the liquid core waveguide into a non-liquid core waveguide having a portion disposed in coupling proximity to the steerable region of the liquid core waveguide. According to an aspect, the coupling step includes at least one of end-fire coupling and evanescent coupling. In an aspect, the method further includes the steps of providing at least another one non-liquid core waveguide in a different coupling proximity to the steerable region of the liquid core waveguide; steering the steerable region of the liquid core waveguide to at least one of a pathway that is not in coupling proximity to the non-liquid core waveguide or at least another one non-liquid core waveguide and that is in coupling proximity to the at least another one non-liquid core waveguide; and respectively, not coupling the light from the liquid core waveguide to either of the non liquid core waveguide or the at least another one of the non-liquid core waveguide or, coupling at least a portion of the light from the steerable region of the liquid core waveguide into the at least another one of the non-liquid core waveguide. According to non-limiting, exemplary aspects, the non-liquid core waveguide is a planar component including a waveguide, an optical ring resonator, an interferometer, a photonic crystal, and a photonic crystal resonator. In an aspect, the step of inputting light comprises inputting light from a solid core waveguide. In an aspect, the non-liquid core waveguide and the at least another one non-liquid core waveguide include a plurality of solid-core optical waveguides. According to an aspect, steering the steerable region of the liquid core waveguide includes controllably directing a fluid stream having an index of refraction lower than the index of refraction of the liquid core against the steerable region of the liquid core waveguide.

In the various embodiments and aspects, input light can be in a wavelength region between about 380 nm to about 1610 nm.

BRIEF DESCRIPTION OF THE DRAWINGS

The features described herein can be better understood with reference to the drawings described below. The drawings are not necessarily to scale, emphasis instead generally being placed upon illustrating the principles of the invention. In the drawings, like numerals are used to indicate like parts throughout the various views.

FIGS. 3(a, b, c) are images showing the dynamics of optical switching between (a) the left solid core output, (b) intermediate the waveguides, and (c) the right solid core output, according to an illustrative aspect of the invention;

FIGS. 4(a, b) illustrate (a) the output power recorded from the solid core waveguides of a device at distances away from perfect alignment between the solid and liquid core waveguides and (b) the dynamic switching output from one of the output waveguides shown in FIG. 3, according to an illustrative aspect of the invention;

FIGS. 5(a, b, c) schematically show aspects of a reconfigurable optofluidic photonic device with surface selectable ring resonators, according to an illustrative aspect of the invention;

FIGS. 6(a, b, c, d) schematically show optical logic circuits using liquid core photonic circuits, according to an illustrative aspect of the invention;

FIGS. 7(a, b) show (a) a general setup of a liquid core/liquid cladding optical waveguide and (b) an on-chip recirculation device, according to illustrative aspects of the invention; and FIGS. 8(a, b) show (a) a conceptual drawing of an on-chip recirculation device and (b) the coupled light at the end of the output solid waveguide, according to illustrative aspects of the invention.

DETAILED DESCRIPTION OF EXEMPLARY EMBODIMENTS

Figure 1:
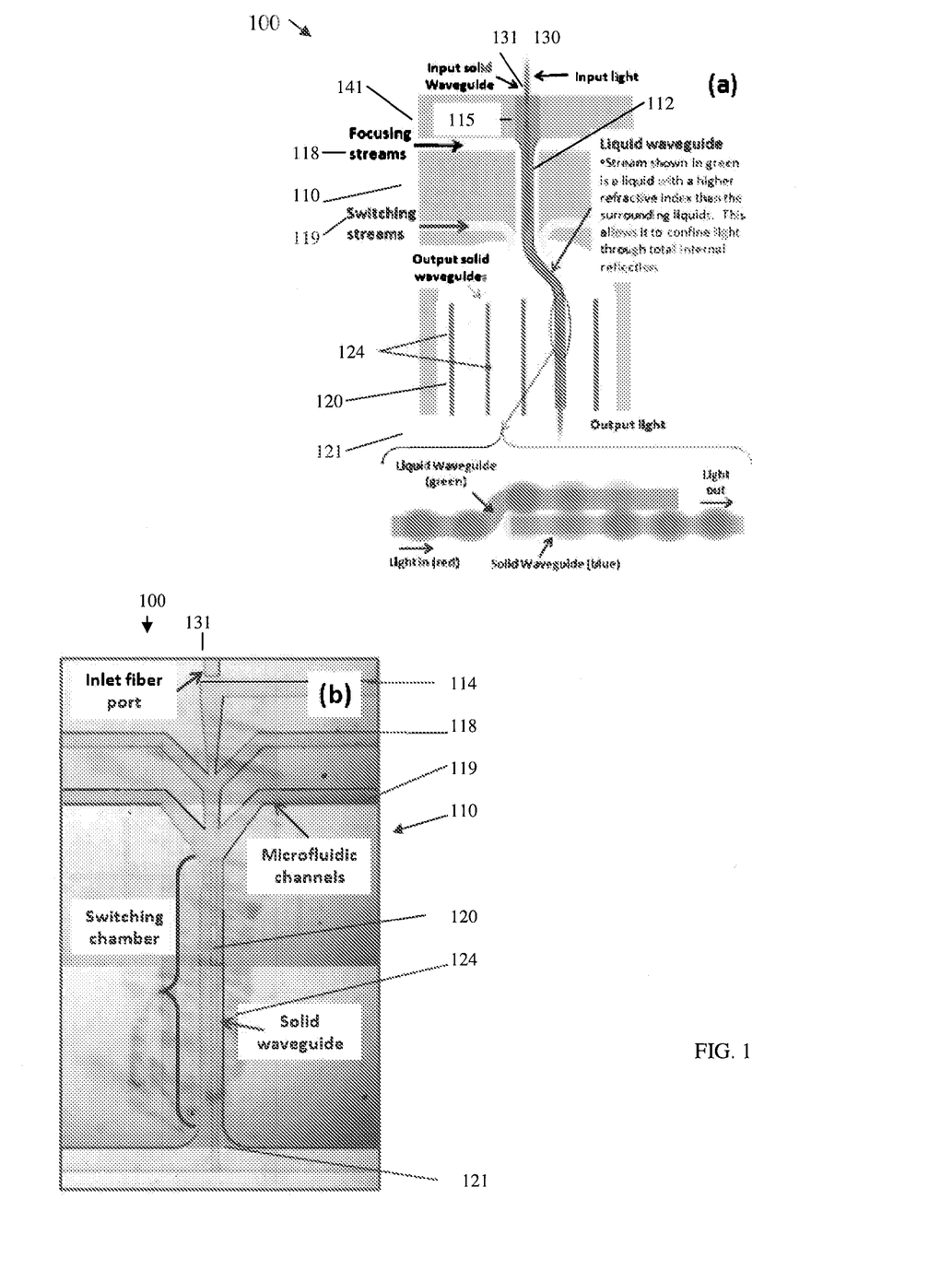
FIG. 1(a) is a schematic diagrams illustrating a reconfigurable photonic apparatus (1×4 optical switching device) according to an exemplary embodiment of the invention.
FIG. 1(b) is an optical image of a reconfigurable photonic apparatus according to an illustrative embodiment of the invention.

FIGS. 1(a) and 1(b), respectively, schematically illustrate a reconfigurable optofluidic apparatus 100 and an image of an integrated optofluidic device 100, in the form of a 1×n (n=5) optical switch, according to a non-limiting, illustrative embodiment of the invention. Briefly, and as known in the art, an optofluidic waveguide comprises a waveguide core fluid surrounded by a cladding, which is typically also a fluid, having a lower index of refraction than the core fluid, contained in a microfluidic channel of the microfluidic device. Light can then propagate in the fluid core via total internal reflection, as in a solid core waveguide such as an optical fiber, for example. Microfluidic devices including microfluidic channels and other microfluidic structures such as valves, pumps, and others are well known in the art.

The apparatus 100 includes a microfluidic component ('chip') 110 having a microfluidic channel 112 disposed therein. The microfluidic channel 112 further includes an inlet 114 for a fluidic waveguide core fluid, a channel pathway 116 for the core fluid, and one or more non-core (cladding, steering) fluid inlets 118, 119. The device also includes a switching chamber 120 that has a cross sectional area that is greater than a corresponding cross sectional area of the channel pathway 116, and an outlet 121 for the core fluid and the non-core-fluid. The apparatus 100 further includes at least portions of at least two non-liquid core waveguides 124 that are positioned in the switching chamber. Light 130 to be propagated through the apparatus is input at a light input 131. The light input may be a solid core waveguide such as, but not limited to an optical fiber or, other means well known in the art for inputting light of a desired wavelength to the fluid core of a fluidic waveguide. As illustrated in the exemplary apparatus of FIG. 1(a), five (n=5) solid core waveguides $124_n$ are parallelly disposed in the switching chamber 120.

Light 130 is input to the chip 110 through an optical fiber that is inserted into a port 131 at the top of the device. Alternatively, light can be coupled into a waveguide on the chip in a number of ways as known in the art. A first microchannel 115 at the top of the chip contains a higher refractive index aqueous solution 140 of $CaCl_2$ (n=1.45), which serves as the fluid waveguide core. Distilled water 141 (n=1.33) is introduced via microchannels 118, to focus the fluid waveguide stream and serve as the fluid cladding for guiding the light 130 in the liquid core/liquid cladding waveguide. Another set of microchannels 119 are provided to introduce streams of distilled water, referred to herein as 'switching streams,' i.e., a steerable region 150 in the chip serves as a transition region between the channel pathway 116 and the switching chamber 120. It will be appreciated that the cladding fluid need not be D.I., but any fluid having a lower refractive index than the solution that is introduced at 115. The microchannels 119 have their outputs in the steering region and by controllably impinging a switching stream of lower index (than the core fluid) fluid against the light-carrying liquid core/liquid cladding waveguide in the steering region, the flow direction of the light-carrying liquid core/liquid cladding waveguide can be manipulated. Thus the light-carrying liquid core/liquid cladding waveguide can be directed to flow over one of the solid core waveguides 124, such that the light 130 propagating in the liquid core/liquid cladding waveguide is end-fire coupled or evanescently coupled into the solid core waveguide from which it can then be output. By controlling the flow characteristics of the switching stream(s), the light-carrying liquid core/liquid cladding waveguide can be directed to flow over any one of the solid core waveguides 124 for out-coupling the light or, between the solid core waveguides (i.e., not in coupling proximity) so that the light is not out-coupled.

Figure 2:
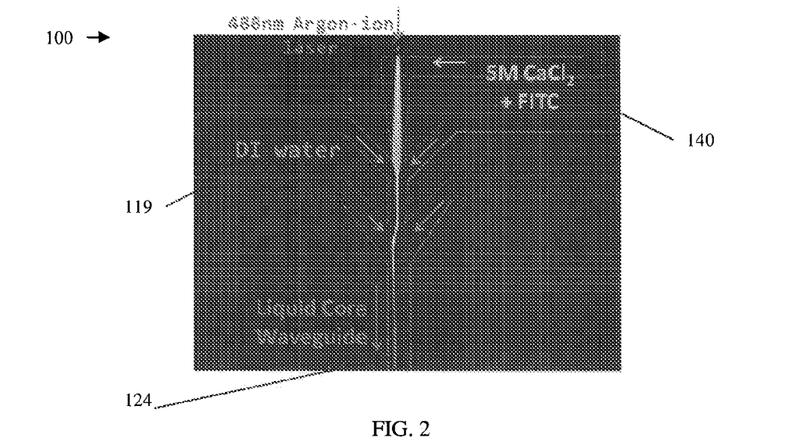
FIG. 2 is an image that shows a dye-doped liquid core waveguide excited with 488 nm light from an Argon-ion laser. The emission from the dye indicates the location of a solid core waveguide in the right switch position, according to an illustrative aspect of the invention.
Figure 3:
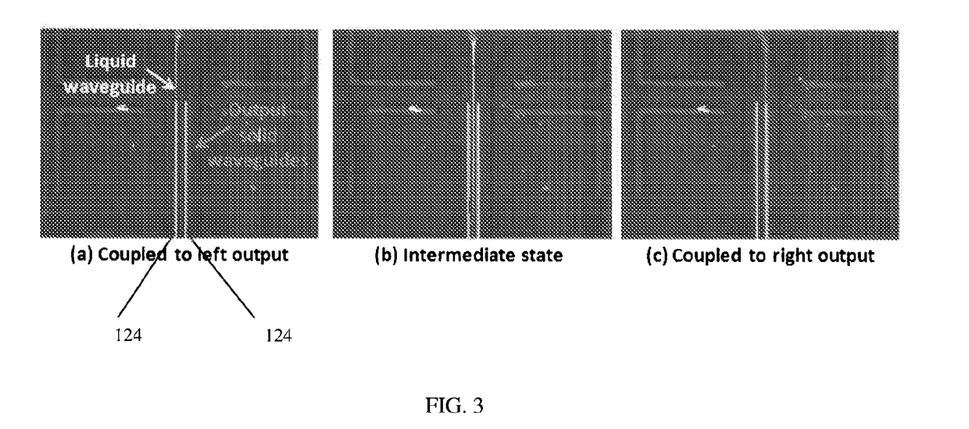

Operation of the apparatus 100 is demonstrated in FIG. 2, in which the liquid core optical waveguide stream 140 is doped with a florescent dye and the stream is excited by 488 nm light from an Argon-ion laser. The florescence emission along the length of the waveguide illustrates the guiding of the light in the liquid core. As is shown in FIGS. 3(a, b, c), by adjusting the flow rate in the switching streams 119, one can position the light-carrying liquid core waveguide stream in, or not in, coupling proximity with one of the solid core output waveguides 124.

Figure 4:
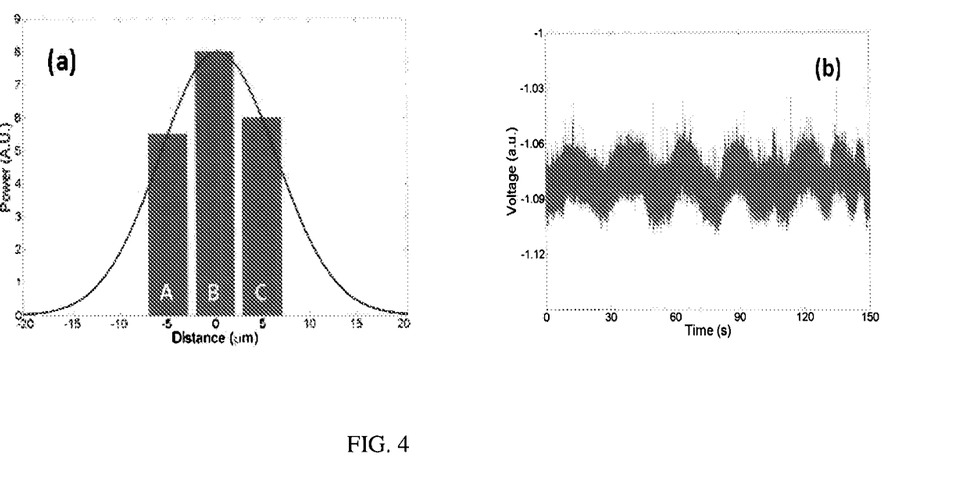

FIG. 4 shows proof-of-concept data obtained with the apparatus 100 for coupling between the liquid core and solid core waveguides. An aspheric lens was placed at the output end of the solid-core waveguide 124 and used to collect and collimate the light into a power meter. As shown in FIG. 4(a), when the liquid core waveguide is positioned immediately over (i.e., in coupling proximity) a solid core waveguide 124, a strong output signal is obtained, which drops off rapidly as the waveguide is moved away (i.e., not in coupling proximity). The total span over which good coupling was observed is approximately 20 μm, suggesting an optical device packing density on that scale. FIG. 4(b) shows results for dynamic switching between the two solid core waveguides (as shown in FIGS. 3(a) and 3(c)). The switching time in the presented results was on the order of 10 seconds. Switching times of less than or equal to 1 millisecond may be achievable.

Table 1 lists comparative data for the expected specifications of a 1×4 switch according to the embodied invention and those for an industry standard SCN 1×4 Switch available from JDSU (complete published specifications from JDSU are available from the following link http://www.jdsu.com/product-literature/scnswitch_ds_cc_ae.pdf). As can be seen in the switching time, drive frequency, and wavelength range categories, the embodied apparatus is expected to provide significant performance improvements over the state of the art.

TABLE 1

| Metric | JDSU SCN 1 × 4 Switch | Optofluidic Switch |
| --- | --- | --- |
| Switching time | 6 ms | 1 ms |
| Drive Frequency | 10 Hz | 100 Hz |
| Insertion Loss | 0.9 dB | Will be Measured |
| Cross Talk | 55 db | Will be Measured |
| Wavelength Range | 1290-1330 nm or 1525-1610 nm | Not restricted |

The optofluidic platform 100 as illustrated in FIG. 1(a) represents a new approach to reconfigurable photonic materials. The device fabrication and integration procedure was carried out as follows. The microfluidic chip was fabricated using a soft-lithography process as set forth in McDonald, J. C., Duffy, D. C., Anderson, J. R., Chiu, D. T., Wu, H. K., Schueller, O. J. A., and Whitesides, G. M., Fabrication of microfluidic systems in poly(dimethylsiloxane), Electrophoresis 21: p. 27-40 (2000) and Duffy, D. C., McDonald, J. C., Schueller, O. J. A., and Whitesides, G. M., Rapid prototyping of microfluidic systems in poly(dimethylsiloxane), Analytical Chemistry 70: p. 4974-4984 (1998). A positive relief master of the microfluidic channel layout was first fabricated in photoresist on a silicon wafer. Liquid poly(dimethylsiloxane), PDMS, was then poured over the master and allowed to cure at 90° C. for 3 hrs, leaving a negative relief layout of the microchannel structure. In an initial prototype as shown in FIG. 1(b), SU-8 based waveguides were used due to their optical transparency over the range of tested wavelengths (488 nm to 1550 nm) and the relative ease of the fabrication procedure. The waveguides were fabricated on a glass wafer using a one step lithography process. After dicing the wafers, the PDMS microfluidic element and the glass photonic system were bonded by exposing the two halves to an air plasma oxidation process and placing them in conformal contact. All fabrication processes were carried out at the Cornell Nanofabrication Facility.

Figure 5:
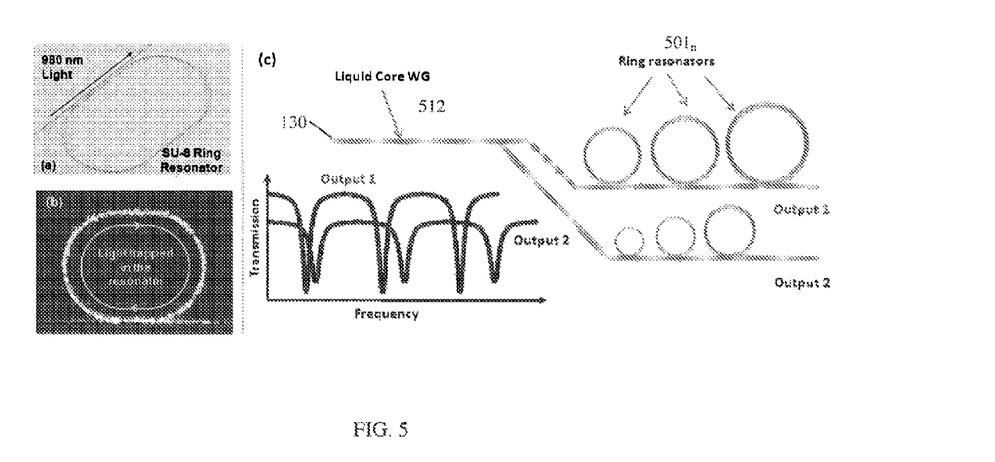

A particular advantage of the embodied optofluidic apparatus and methods is the ability to completely reconfigure the optical layout simply by redirecting the local switching stream flow rates. For example, as shown with reference to FIG. 5, one or more optical ring resonators $501_n$ can be integrated into the device, wherein the device is now configured as a tunable optical filter. For multiple ring resonators, the rings may have different sizes as depicted in FIG. 5(c). The ring resonators need not be circular per se, and may include elliptical and race-track geometries, as well as others known in the art.

As shown in regard to FIGS. 5(a, c), multiple SU-8 ring resonators $501_n$ were fabricated onto the bottom substrate in such a way that they can be selected by the liquid core waveguides either individually or as a group. When a liquid core waveguide passes over a ring, the light 130 will be evanescently coupled into the ring in the same manner as it would for a solid core waveguide. If the liquid core waveguide is excited at a wavelength that is resonant with the ring (FIG. 5(b); i.e., the effective path length for light travelling around the ring is an integer multiple of the wavelength of the light such that it destructively interferes with itself), then that wavelength will be selected out of the transmission spectrum as shown in the transmission vs. frequency graphs as part of FIG. 5(c). This demonstrates the ability to integrate advanced optical functionality into a reconfigurable optofluidic photonic apparatus. More specifically, the embodied apparatus and method afford significantly enhanced flexibility over earlier works in which the optical resonance of a device could be tuned microfluidically by changing the refractive index in the cover region, thereby changing the effective refractive index of the ring and by extension the wavelength of the light that would resonate within it. In the embodied approach, an arbitrary set of rings can be selected, thereby providing the opportunity to define and tune an arbitrary output spectrum (as opposed to simply shifting an existing one). Furthermore, the embodied approach, in being the first to use microfluidic liquid core waveguides to transport the light, enable the simple integration of tunable optical filtering with the additional switching functionality described above and redefineable optical logic functionality as described below, into a single device.

It will be appreciated by those skilled in the art that the one or more ring resonators referred to above are not the only non-liquid core waveguide components into which light propagating in the liquid core waveguide can couple to; rather, any planar device including, but not limited to, an interferometer, a photonic crystal, and a photonic crystal resonator would be suitable.

Figure 6:
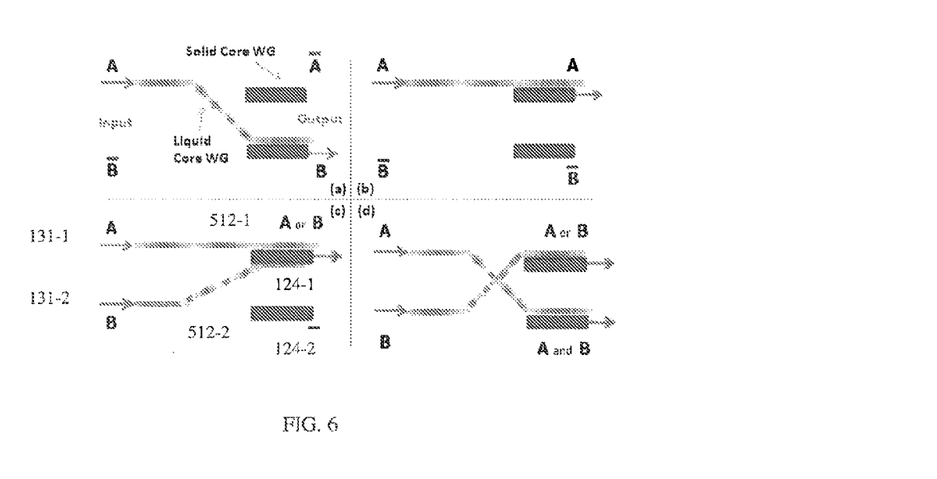

FIGS. 6(a, b, c, d) schematically illustrate the basic layout of four redefineable optofluidic logic circuits that can perform arbitrary logic operations (a) AB, (b) AA, (c) A or B, and (d) A and B. According to a non-limiting, illustrative aspect, two liquid core waveguides 612-1, 612-2 are excited by two input optical fibers 131-1, 131-2 embedded into the chip upstream of the logic switch (identical to the way light is coupled into the chip shown in FIG. 5) with signals A, B. Two downstream solid core output waveguides 124-1, 124-2 are disposed in a switching chamber (not shown) and output the respective logical signal combinations shown.

In all of the embodiments and aspects, the input light can be in the spectral region from between about 320 nm to about 1610 nm, which encompass the C, L, and M telecommunication wavebands.

Since the reported introduction of liquid core/liquid cladding optical wave guides (D. B. Wolfe, R. S. Conroy, P. Garstecki, B. T. Mayers, M. A. Fischbach, K. E. Paul, M. Prentiss, and G. M. Whitesides, Dynamic control of liquid-core/liquid-cladding optical waveguides, Proceedings of the National Academy of Sciences of the United States of America, 101, 12434 (2004)), many studies took advantage of the reconfigurability of its shape and the ease of change in optical properties. However, although the liquid waveguide has novel features that cannot be achieved in current solid, generally silicon-based optical waveguides, the liquid waveguide has not been utilized as a component in optical chips. One of the major reasons for this stems from the nature of these traditional liquid waveguide systems, which rely on the continuous supply and draining of liquids. A solution to this problem is embodied in an apparatus and method for recirculating the liquids (core, cladding) and thus enabling a liquid waveguide chip to be used for an indefinite period of time without requiring a continuous supply of liquids.

Figure 7:
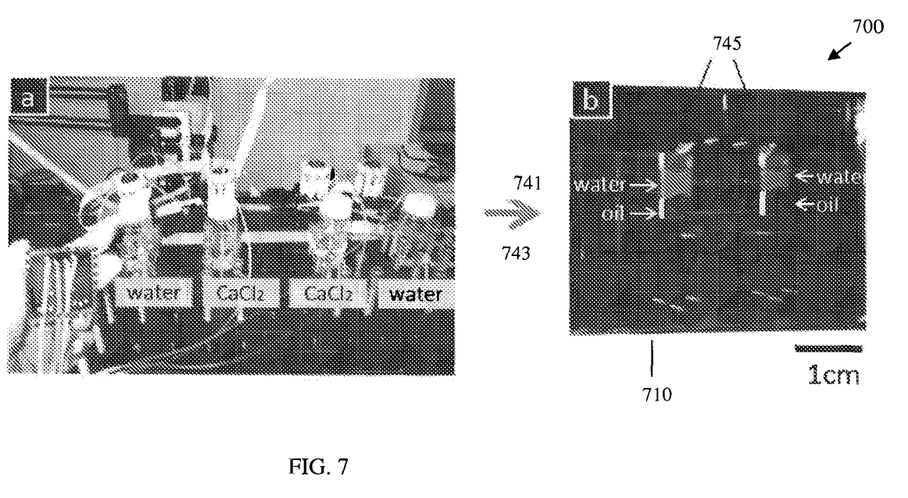

Typically, liquid core/liquid cladding waveguides use miscible liquids as the core and cladding liquids (e.g., $CaCl_2$ solution and water). Since these miscible liquids are mixed after forming the liquid waveguide, reuse of the mixed liquid is not practical. As such, these systems utilize external storage bottles to supply and drain liquids to and from the chip, respectively, as shown in FIG. 7(a). Furthermore the possible leakage of these liquids can cause damage to other optical and electronic components.

FIG. 7(b) shows an on-chip optofluidic recirculation system 700, according to a non-limiting, exemplary aspect of the invention. The system 700 uses immiscible liquids, water 741 as a core liquid and Flourinert oil 743 as a cladding liquid, which are completely sealed and separated in reservoirs 745 and continuously circulate inside the 3 cm×4 cm chip 710. As shown in FIG. 7(b), the chip is advantageously vertically oriented and the immiscible liquids separate in the reservoirs due to their respective densities.

Figure 8:
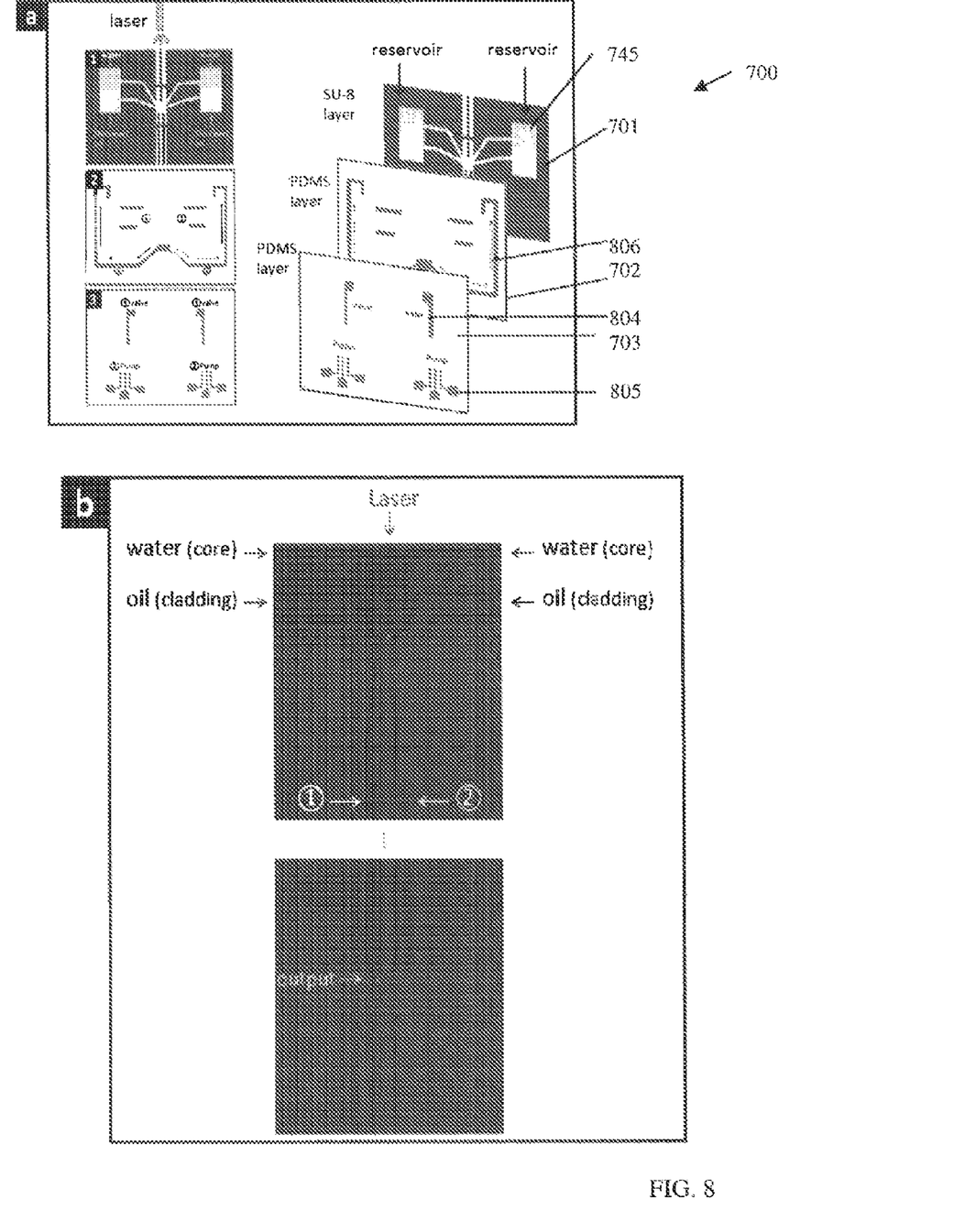

FIG. 8(a) schematically illustrates the exemplary recirculating optofluidic system 700 shown in FIG. 7(b) and the fabrication procedure. The system has three layers 701, 702, 703. The first layer 701 is made of SU-8 photoresist and is fabricated on a silicon substrate. It includes the microfluidic channels as shown in FIGS. 1(b) and 2, the reservoirs 745, which are fluidically connected to the focusing streams 118 and the switching streams 119 (FIG. 1(a)), and the solid core waveguides for inputting and outputting light to and from the device. The second layer 702 and the third layer 703 are each made of PDMS (polydimethylsiloxane) and contain the pumping system (valves 804, monolithic elastomeric pumps 805, channels 806) to recirculate the immiscible liquids. In the instant exemplary aspect, PDMS layers 702 and 703 are fabricated and assembled with materials and via techniques well known in the microfluidic art (see, e.g., Unger et al., Monolithic Microfabricated Valves and Pumps by Multilayer Soft Lithography, Science, 288, 113, (2000)). It may also be possible to construct the device using non-elastomeric microfluidic components as taught, for example, in U.S. Pat. No. 7,608,160.

The layers are bonded and sealed, containing liquids to form the liquid waveguide. Light is input to the optofluidic chip through the input solid core waveguide, is coupled into the liquid waveguide and, then into the output solid core waveguide. Since the light starts from a solid waveguide and ends at a solid waveguide, the solid to liquid to solid coupling advantageously enables one to connect the liquid core waveguide to solid core wave guides that are connected to other solid elements having different functionalities (e.g., signal amplifier and modulator). As a result, the embodied device makes it possible to utilize the optofluidic waveguide as a unique optical switch to build a total optical network.

FIG. 8(b) shows a result of the coupled light at the end of the output solid core waveguide and demonstrates that immiscible liquids can guide and switch the light without mass diffusion, which may occur in miscible liquid optical waveguiding systems.

The use of the terms "a" and "an" and "the" and similar references in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed. No language in the specification should be construed as indicating any non-claimed element as essential to the practice of the invention.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

We claim:

1. A reconfigurable optofluidic apparatus, comprising:
   a microfluidic chip including a microfluidic channel disposed therein, wherein the microfluidic channel includes:
   an inlet for a liquid core waveguide fluid
   a channel pathway for the liquid core waveguide fluid;
   a plurality of non-core waveguide fluid inlets;
   a switching chamber, wherein the switching chamber has a cross sectional area that is greater than a corresponding cross sectional area of the channel pathway; and
   an outlet for the liquid core waveguide fluid and the non-core-fluid;
   a plurality of non-liquid core waveguides disposed at least in part in the switching chamber; and
   a light input port.

2. The apparatus of claim 1, wherein the plurality of non-liquid core waveguides are solid core waveguides disposed in a parallel spaced relationship.

3. The apparatus of claim 1, wherein the plurality of non-liquid core waveguides includes at least a portion of at least one of a waveguide, an optical ring resonator, an interferometer, a photonic crystal, and a photonic crystal resonator.

4. The apparatus of claim 1, wherein the liquid core waveguide fluid comprises a cladding fluid having an index of refraction that is lower than the index of refraction of the core fluid.

5. The apparatus of claim 1, wherein the plurality of non-core-fluid inlets further comprises a plurality of liquid waveguide core-focusing channels and a plurality of liquid core waveguide steering channels.

6. The apparatus of claim 1, wherein the plurality of non-liquid core waveguides includes a plurality of optical ring resonators having at least two different ring sizes.

7. The apparatus of claim 1, wherein the apparatus is a 1×n optical switch.

8. The apparatus of claim 1, wherein the microfluidic component further includes a second microfluidic channel that further includes:
   a second inlet for the liquid core waveguide fluid
   a second channel pathway for the liquid core waveguide fluid; and
   a second plurality of non-core-fluid inlets,
   wherein the second microfluidic channel is in fluid connection with the switching chamber.

9. The apparatus of claim 8, wherein the apparatus is an optical logic circuit.

10. The apparatus of claim 1, further comprising:
    a self-contained, fluid recirculation system integrated in the apparatus, including:
    a reservoir in fluid connection with the microfluidic channel;
    a fluid recirculation channel in fluid connection with the reservoir; and
    a microfluidic pumping system.

11. The apparatus of claim 10, wherein the microfluidic chip is in the form of a first layer of the apparatus and includes the reservoir, further wherein the fluid recirculation channel is disposed on a second layer of the apparatus, and further wherein the microfluidic pumping system is disposed on a third layer of the apparatus.

12. The apparatus of claim 10, further comprising a liquid core waveguide fluid and a non-core waveguide fluid, which are immiscible.

13. The apparatus of claim 12, wherein the liquid core waveguide fluid is water and the non-core waveguide fluid is Flourinert oil.

14. An optofluidic switching method, comprising:
    inputting light into a core of a liquid core waveguide having a given propagation pathway that includes a steerable region;
    propagating the light in the liquid core waveguide;

coupling at least a portion of the light from the liquid core waveguide into a non-liquid core waveguide having a portion disposed in coupling proximity to the steerable region of the liquid core waveguide, wherein coupling includes at east one of end-fire coupling and evanescent coupling;

providing at least another one non-liquid core waveguide in a different coupling proximity to the steerable region of the liquid core waveguide;

steering the steerable region of the liquid core waveguide to at least one of a pathway that is not in coupling proximity to the non-liquid core waveguide or at least another one non-liquid core waveguide and that is in coupling proximity to the at least another one non-liquid core waveguide; and respectively, not coupling the light from the liquid core waveguide to either of the non-liquid core waveguide or the at least another one of the non-liquid core waveguide or, coupling at least a portion of the light from the steerable region of the liquid core waveguide into the at least another one of the non-liquid core waveguide.

15. The method of claim 14, wherein the non-liquid core waveguide is a planar device including at least one of a waveguide, an optical ring resonator, an interferometer, a photonic crystal, and a photonic crystal resonator.

16. The method of claim 14, wherein the step of inputting light comprises inputting light from a solid core waveguide.

17. The method of claim 14, wherein the at least another one non-liquid core waveguide is a planar device including at least one of a waveguide, an optical ring resonator, an interferometer, a photonic crystal, and a photonic crystal resonator.

18. The method of claim 14, wherein the non-liquid core waveguide and the at least another one non-liquid core waveguide comprises a plurality of solid-core optical waveguides.

19. The method of claim 14, wherein the pathway of the steerable region comprises a channel of a microfluidic device in which at least a portion of the non-liquid core waveguide is disposed.

20. The method of claim 14, wherein the pathway of the steerable region comprises a channel of a microfluidic device in which at least a portion of the non-liquid core waveguide and at least a portion of the at least another one non-liquid core waveguide are disposed.

21. The method of claim 14, wherein steering the steerable region of the liquid core waveguide comprises controllably directing a fluid stream having an index of refraction lower than the index of refraction of the liquid core against the steerable region of the liquid core waveguide.

22. The method of claim 14, further comprising inputting light in a wavelength region between about 320 nanometers (nm) to about 1610 nm.

23. An optofluidic switching method, comprising:

inputting light into a core of a liquid core waveguide having a given propagation pathway that includes a steerable region;

propagating the light in the liquid core waveguide;

providing at least a portion of a non-liquid core waveguide in coupling proximity to the steerable region of the liquid core waveguide;

coupling at least a portion of the light from the steerable region of the liquid core waveguide into the non-liquid core waveguide;

providing at least a portion of at least another one non-liquid core waveguide in a coupling proximity of the steerable region of the liquid core waveguide;

steering the steerable region of the liquid core waveguide to at least one of a pathway that is not in coupling proximity to the non-liquid core waveguide or the at least another one non-liquid core waveguide and that is in coupling proximity to the at least another one non-liquid core waveguide; and, respectively, not coupling the light from the liquid core waveguide to either of the non-liquid core waveguide or the at least another one of the non-liquid core waveguide or, coupling at least a portion of the light from the liquid core waveguide into the at least another one of the non-liquid core waveguide.

24. The method of claim 23, wherein coupling includes at least one of end-fire coupling and evanescent coupling.

25. The method of claim 23, wherein the non-liquid core waveguide is a planar device including at least one of a waveguide, an optical ring resonator, an interferometer, a photonic crystal, and a photonic crystal resonator.

26. The method of claim 23, wherein the step of inputting light comprises inputting light from a solid core waveguide.

27. The method of claim 23, wherein the non-liquid core waveguide and the at least another one non-liquid core waveguide comprises a plurality of solid-core optical waveguides.

28. The method of claim 23, wherein the pathway of the steerable region comprises a channel of a microfluidic device in which at least a portion of the non-liquid core waveguide is disposed.

29. The method of claim 23, wherein the pathway of the steerable region comprises a channel of a microfluidic device in which at least a portion of the non-liquid core waveguide and at least a portion of the at least another one non-liquid core waveguide are disposed.

30. The method of claim 23, wherein steering the steerable region of the liquid core waveguide comprises controllably directing a fluid stream having an index of refraction lower than the index of refraction of the liquid core against the steerable region of the liquid core waveguide.

31. The method of claim 23, further comprising inputting light in a wavelength region between about 320 nm to about 1610 nm.

\* \* \* \* \*